United States Patent
Foos

(10) Patent No.: US 9,549,860 B2
(45) Date of Patent: Jan. 24, 2017

(54) DENTAL ISOLATOR

(71) Applicant: Valerie Lee Foos, Big Rapids, MI (US)

(72) Inventor: Valerie Lee Foos, Big Rapids, MI (US)

(*) Notice: Subject to any disclaimer, the term of this patent is extended or adjusted under 35 U.S.C. 154(b) by 139 days.

(21) Appl. No.: 14/544,604

(22) Filed: Jan. 26, 2015

(65) Prior Publication Data

US 2016/0213448 A1    Jul. 28, 2016

(51) Int. Cl.
| | |
|---|---|
| A61C 5/12 | (2006.01) |
| A61F 13/53 | (2006.01) |
| A61F 13/20 | (2006.01) |
| A61C 15/04 | (2006.01) |

(52) U.S. Cl.
CPC .......... *A61F 13/53* (2013.01); *A61F 13/2008* (2013.01); *A61C 15/041* (2013.01); *A61F 2013/530029* (2013.01)

(58) Field of Classification Search
CPC ... A61C 15/041; A61C 19/001; A61C 19/003; A61C 19/063; A61C 5/04; A61C 5/122; A61F 13/2008; A61F 13/53; A61F 2013/530029
See application file for complete search history.

(56) References Cited

U.S. PATENT DOCUMENTS

| | | | |
|---|---|---|---|
| 2,274,814 A | 3/1942 | West | |
| 4,705,514 A * | 11/1987 | Barnard | ............... A61F 13/2008 433/136 |
| 2012/0322029 A1 | 12/2012 | Foos | |

* cited by examiner

*Primary Examiner* — George Manuel
(74) *Attorney, Agent, or Firm* — Timothy S. Stevens; Karen L. Kimble

(57) ABSTRACT

A dental isolator in the form of a U-shaped absorbent member having a first portion and a second portion disposed on either side of a third central portion and a retainment member, which retainment member transversely engages both the first portion and the second portion of the absorbent member, the retainment member being adapted to fit between adjacent teeth of a dental patient, the first portion of the U-shaped absorbent member being adapted to be disposed on the internal side of the teeth of a dental patient between the teeth and the tongue of the patient, the second portion of the U-shaped absorbent member to be disposed between the cheek and the mucobuccal fold of the patient with the central portion of the U-shaped absorbent member surrounding a rear tooth of the patient, the distal end of the second portion of the U-shaped absorbent member being tapered.

6 Claims, 1 Drawing Sheet

DENTAL ISOLATOR

BACKGROUND OF THE INVENTION

The chewing surface of one's teeth, particularly one's permanent molars are highly textured, which makes cleaning these teeth difficult. The chewing surfaces of these teeth have projections and recessions which form the occlusal surface of the molars. Since the occlusal surfaces of the permanent molars are where the chewing occurs, food particles and plaque can build up in these recessions commonly known in the art as pits and fissures. The pits and fissures are difficult to clean due to their small size, and, if food and plaque are allowed to build up in these areas, tooth decay or caries can develop. Specifically, caries occur largely on the occlusal plane of the tooth. The occlusal plane or surface is generally considered the biting surface of a tooth which actuates against and with an antagonist tooth on an opposing arch. Dental pits and fissures of various shapes are located on this surface where food residue or intraoral bacterial are deposited and can lead to the formation of caries. The permanent molars are the most susceptible teeth in the mouth for dental caries. Hence, the molars are preferably sealed shortly after erupting and before dental caries can begin.

In an effort to prevent caries from forming in the pits and fissures of the occlusal surface of a tooth, the tooth can be sealed with a pit and fissure sealant which helps to protect the tooth. In a pit and fissure sealant process, a dental pit and fissure sealant fills the narrow and deep pits and fissures. In this way, the pit and fissure sealant prevents bacteria or food residue from gathering in the difficult to clean pits and fissures so as to prevent the development of caries. Dental pit and fissure sealants of various types are known in the art and are generally comprised of a Bis-GMA resin-based sealant. A dental pit and fissure sealant process generally takes place while the patient has a permanent or mixed dentition in which the permanent dentition is comprised of permanent teeth and the mixed dentition is comprised of both primary teeth and permanent teeth. Generally, this process takes place in patients through the age of 15 on teeth that do not have cavities. The teeth, particularly the molars, of patients in this age group have pits and fissures which consist of ridges, such as triangular ridges and transverse ridges, which form from the cusp of the molars and premolars to the center part of the tooth's occlusal surface. Oblique ridges and grooves are also found on molars, which create places for food and bacteria to be deposited. A rounded depression, such as a fossa, can be found on the surface of the tooth and is generally formed by the converging of different ridges at a central point in the bottom of a depression where there is a junction of grooves, such as the developmental and supplemental grooves. This conforms to a central pit, which is often the site of tooth decay.

In applying a pit and fissure sealant, a dentist or dental hygienist will generally clean the tooth requiring the sealant with either air abrasive or mildly acidic solution, or both, to score or etch the surface of the tooth such that the surface becomes rough, thereby making it easier for the pit and fissure sealant to adhere properly. Keeping the tooth dry during this procedure is of utmost importance as the pit and fissure sealant might not adhere properly to the tooth surface if saliva and other forms of moisture are on the tooth surface when the sealant is applied.

Thus, a tooth should be thoroughly dried, etched, rinsed and dried again and kept isolated from any moisture contamination during a pit and fissure sealant procedure. The liquid sealant material is then placed into the pits and fissures, covering the occlusal surface of the molars. A high intensity curing light (reaction accelerator) is then directed at the occlusal surface to polymerize the sealant material. During the application of the curing light, the tooth must be isolated and dry. The present invention relates to a dental isolator which isolates a tooth or multiple teeth to be sealed and keeps the teeth dry during the application and cure of the pit and fissure sealant.

The dental isolators of U.S. Pat. No. 2,274,814 and US Patent Application Publication No. US 2012/0322029 disclosed a significant advance in the art. These dental isolators comprised U-shaped devices having an internal side and an external side and a retainment member between the sides, the retainment member to be disposed between adjacent teeth of a dental patient. However, a remaining problem with these dental isolators is the tendency of the distal end of the external side of the dental isolator to rise up and permit saliva to contaminate one or more teeth during a dental procedure.

SUMMARY OF THE INVENTION

The dental isolator of the instant invention is a significant improvement over the dental isolators of the type disclosed in U.S. Pat. No. 2,274,814 and US Patent Application Publication No. US 2012/0322029. The problem of the distal end of the external side of the dental isolator of this type to rise up and permit saliva to contaminate one or more teeth is solved in the instant invention by tapering said distal end. Tapering said distal end significantly reduces the tendency of the external side of the dental isolator to rise up and permit saliva to contaminate one or more teeth during dental procedures such as the application of sealants and the filling of cavities.

More specifically, the present invention comprises a dental isolator for use in the mouth of a dental patient, the dental isolator comprising an absorbent member having an internal side and an external side and a flexible portion disposed between the internal side and the external side. The internal side is configured to be disposed on the lingual side of the patient's mouth and the external side is configured to be disposed on the buccal side of the patient's mouth, the external side being tapered at its distal end. The dental isolator also comprises at least one retainment member which is coupled to the internal side and the external side of the absorbent member in assembly. The retainment member of the dental isolator is configured to fit between adjacent teeth of a dental patient.

In another embodiment, the instant invention is a method for treating a dental patient requiring application of sealants to the patient's teeth or the filling of cavities of the patient's teeth which method comprises the steps of: (a) adjusting the dental isolator of the instant invention as needed so that the second portion of the U-shaped absorbent member of the dental isolator is the desired fit to be disposed between the cheek and the mucobuccal fold of the patient as needed for the patient; and (b) inserting the adjusted dental isolator of step (a) into the patient's mouth, the retainment member being placed between adjacent teeth of the dental patient, the first portion of the U-shaped absorbent member being adapted to be disposed on the internal side of the teeth of the dental patient between the teeth and the tongue of the patient, the second portion of the U-shaped absorbent member to be disposed between the cheek and the mucobuccal fold of the patient to prevent saliva contamination of the isolated tooth.

DETAILED DESCRIPTION OF THE INVENTION

Figure 5:
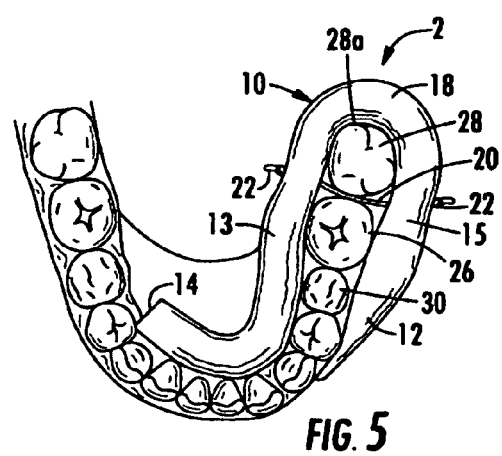
FIG. 5 is a top plan view of the present invention as installed in the mouth of a patient.

For the purposes of description herein, the terms "upper," "lower," "right," "left," "rear," "front," "vertical," "horizontal," and derivatives thereof shall relate to the invention as oriented in FIG. 5 from the point of view of the patient. However, it should be understood that the invention may assume various alternative orientations, except where expressly specified to the contrary. It is also to be understood that the specific devices and processes illustrated in the attached drawings, and described in following specification, are simply exemplary highly preferred embodiments. Hence, specific dimensions and other physical characteristics relating to the embodiments disclosed herein are not to be construed as limiting, unless expressly stated otherwise. In addition, the term "distal" herein should not be understood as referring to the patient. The term "distal" herein refers to the device of the instant invention.

Figure 1:
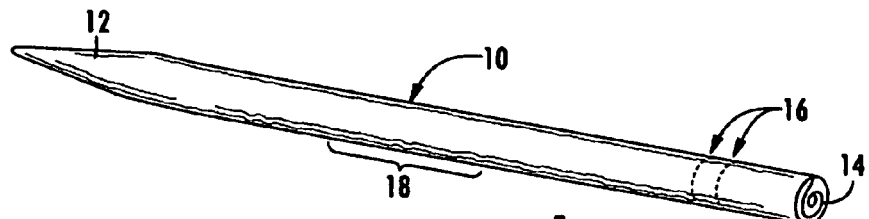
FIG. 1 is a perspective view of an absorbent member used in conjunction with the present invention.

Referring to FIG. 1, the reference numeral 10 generally designates an absorbent member as used in the present invention. As shown in FIG. 1, the absorbent member 10 has a first portion with a first tapered end 12 and a second portion with a second end 14 as well as a flexible third portion 18 disposed between the first and second portions. As shown in FIG. 1, the absorbent member 10 can be trimmed at various locations, such as locations 16 indicated by dotted lines on the body portion of absorbent member 10, which will then create new second end 14. In this way, absorbent member 10 is adjustable in length, providing a custom-tailored absorbent member for use with a patient as further described below.

The absorbent member 10 is made of any suitable material which is approved for dental use, which is capable of absorbing moisture and is ultimately used to keep a tooth isolated and dry during, for example, the application of a pit and fissure sealant or other dental procedure such as the filling of a cavity. The absorbent member 10, as shown in FIG. 1, is preferably in the form of an absorbent cotton roll which is trimmable, flexible, and absorbent for use with the present invention. It is also contemplated that the absorbent member 10 can have different colors as well as different flavoring agents added to the absorbent member material in an effort to make, for example, the pit and fissure sealant process more enjoyable for the patient. Different colors of absorbent members 10 can also indicate the general size of the absorbent member being used such that, for example, child and adult sizes can easily be differentiated.

Figure 2:
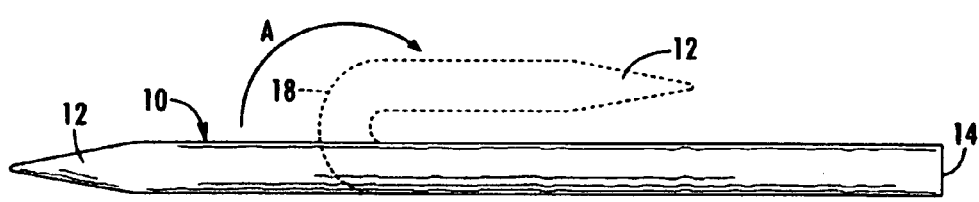
FIG. 2 is a top plan view of the absorbent member of FIG. 1.

Referring to FIG. 2, the absorbent member 10 is shown curved along flexible portion 18, such that, as shown in FIG. 2, end 12 is moved toward end 14 along the pathway indicated by arrow A, such that the absorbent member 10 takes on a U-shaped configuration as indicated by the dotted lines in FIG. 2. While portion 18 of the absorbent member 10 is specifically identified as a flexible portion, it is contemplated that the entirety of the absorbent member 10 can be made from a flexible absorbent material, preferably the cotton roll as described above, so that the device can be adjusted to different dental spacing.

Figure 3:
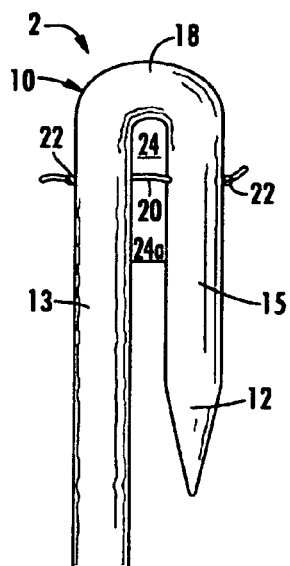
FIG. 3 is a top plan view of a dental isolator of the present invention.

Referring to FIG. 3, the reference numeral 2 generally designates a dental isolator or tooth isolation device of the present invention wherein the absorbent member 10 is bent at flexible portion 18 to create an internal side 13 and an external side 15 corresponding to second and first ends 14, 12, respectively. Disposed between and connecting external side 15 and internal side 13, a dental isolator retainment member 20 is shown. In the embodiment shown in FIG. 3, the dental isolator retainment member 20 is in the form of a polymeric nylon-type dental floss which has abutment members or coupling members 22 coupled to and located on the outside of internal side 13 and external side 15, which keep the absorbent member 10 in a U-shaped configuration and create a tooth isolation zone 24. The abutment members 22 of the dental isolator retainment member 20 are shown in FIG. 3 as knots tied in the floss or nylon retainment member 20. While the embodiment shown in FIG. 3 uses knots 22 in the floss or nylon retainment member 20, it is contemplated that any abutment-type member would work in this arrangement (such as the T-ended monofilament devices commonly used to fix tags to new clothing), so long as the abutment member 22 engages and keeps the absorbent member 10 in the U-shaped configuration, as shown in FIG. 3. Further, it is contemplated that the retainment member 20 can be a one piece elastomeric member having first and second coupling members.

Figure 4:
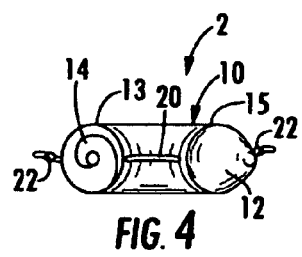
FIG. 4 is an elevational view of the embodiment shown in FIG. 3.

As shown in FIG. 4, the dental isolator 2 has an absorbent member 10 with first and second ends 12, 14 with the dental isolator retainment member 20 disposed therebetween, wherein the dental isolator retainment member 20 is configured to fit between adjacent teeth of a patient as further described below. It is further contemplated that the dental isolator retainment member 20 can be colored for identification purposes or flavored for the comfort of the patient in which it is installed.

Referring now to FIG. 5, a dental isolator 2 of the instant invention is shown having an absorbent member 10 in which internal side 13 and external side 15 such that the internal side 13 projects medially and lingually along a patient's mouth around to the front of the mouth ending near the patient's canines and incisors. It is highly preferred (but not critical) that the internal side 13 of the dental isolator 2 be long enough as shown in FIG. 5 to be positioned over the salivary glands under the tongue to assist in moisture control and to keep the internal side 13 of the dental isolator 2 in place. Similarly, in this embodiment, the exterior side 15 of the absorbent member 10 extends around the patients mouth facially between the cheek and the mucobuccal fold of the patient and terminates at tapered end 12. In this configuration, it will be noted that pre-molar 30, first molar 26 and second molar 28 are protected from moisture by internal side 13 and external side 15 and flexible portion 18 which wraps around the back end 28a of second molar 28. In this embodiment, dental isolator retainment member 20 is disposed between first and second molars 26 and 28, thereby keeping the dental isolator 2 in place during the various steps of a dental process. When the dental isolator of the instant invention is used for a younger patient not having a second molar, then the dental isolator of the instant invention is wrapped around the back end of the first molar and the retainment member is disposed between the first molar and the pre-molar.

The above description is considered to be of the preferred embodiment only. Modifications of the disclosed dental isolator will occur to those skilled in the art and to those who make or use the disclosed dental isolator. Therefore, it is understood that the embodiment shown in the drawings and described above are merely for illustrative purposes and not intended to limit the scope of the invention. For example, the specific shape of the tapered end of the dental isolator of the present invention is not critical. The shape of the tapered end of the dental isolator of the present invention can, for example and without limitation there to, be a symmetrical cone, an asymmetrical cone or an angle cut tube. The tapered end of the dental isolator of the present invention can be conveniently made when the device comprises a cotton tube by first forming a device like that shown in FIG. 3 but with each end being blunt and then pulling one end away so that the remaining torn end is tapered and so that the remaining torn end is the correct length to fit the patient's mouth.

Comparative Example

The dental isolation device of US Patent Application Publication No. US 2012/0322029 is placed in the mouth of a patient to isolate the left lower permanent molars of the patient for a pit and fissure sealant procedure. Said permanent molars are thoroughly dried, etched, rinsed and dried again. However, the exterior end of the device rises up in the mouth of the patient and one of said permanent molars is contaminated with saliva during the application of the sealant.

Example

The dental isolation device of the instant invention is placed in the mouth of a patient as shown in FIG. 5 to isolate the left lower permanent molars of the patient for a pit and fissure sealant procedure. Said permanent molars are thoroughly dried, etched, rinsed and dried again. The tapered exterior end of the device remains between the cheek and the mucobuccal fold of the patient and said permanent molars remain uncontaminated by saliva. The tooth is coated with a UV curing sealant. The tooth remains uncontaminated by saliva. The coated tooth remains uncontaminated by saliva as the coating is irradiated with UV light to cure the sealant coating on the tooth.

What is claimed is:

1. A tooth isolation device comprising: a U-shaped absorbent member having a first portion and a second portion disposed on either side of a third central portion and a retainment member, which retainment member transversely engages both the first portion and the second portion of the absorbent member, the retainment member being adapted to fit between adjacent teeth of a dental patient, the first portion of the U-shaped absorbent member being adapted to be disposed on the internal side of the teeth of a dental patient between the teeth and the tongue of the patient, the second portion of the U-shaped absorbent member to be disposed between the cheek and the mucobuccal fold of the patient with the central portion of the U-shaped absorbent member surrounding a rear tooth of the patient, the distal end of the second portion of the U-shaped absorbent member being tapered.

2. The tooth isolation device as defined in claim 1, wherein the absorbent member comprises a cotton roll.

3. The tooth isolation device as defined in claim 2, wherein the retainment member comprises dental floss.

4. The tooth isolation device as defined in claim 1, wherein the retainment member comprises dental floss.

5. A method for treating a dental patient requiring application of sealants to the patient's teeth or the filling of cavities of the patient's teeth which method comprises the steps of: (a) adjusting the dental isolator as claimed in claim 1 as needed so that the second portion of the U-shaped absorbent member of the dental isolator as claimed in claim 1 is the desired fit to be disposed between the cheek and the mucobuccal fold of the patient as needed for the patient; (b) inserting the adjusted dental isolator of step (a) into the patient's mouth, the retainment member being placed between adjacent teeth of the dental patient, the first portion of the U-shaped absorbent member being adapted to be disposed on the internal side of the teeth of the dental patient between the teeth and the tongue of the patient, the second portion of the U-shaped absorbent member to be disposed between the cheek and the mucobuccal fold of the patient, the tapered end of the second portion of the U-shaped absorbent member reducing the tendency of said second portion from rising up to cause saliva contamination of a tooth isolated by the device claimed in claim 1.

6. The method of claim 5, wherein an isolated tooth is dried, etched, rinsed, dried, coated with a UV curing sealant and then irradiated with UV light.

\* \* \* \* \*